US012622773B2

(12) United States Patent
Fisker et al.

(10) Patent No.: US 12,622,773 B2
(45) Date of Patent: *May 12, 2026

(54) DETECTING AND MONITORING DEVELOPMENT OF A DENTAL CONDITION

(71) Applicant: 3SHAPE A/S, Copenhagen K (DK)

(72) Inventors: Rune Fisker, Virum (DK); Henrik John Brandt, Copenhagen NV (DK); Alen Bogdanic, Brøndby Strand (DK)

(73) Assignee: 3Shape A/S, Kobenhavn K (DK)

( * ) Notice: Subject to any disclaimer, the term of this patent is extended or adjusted under 35 U.S.C. 154(b) by 38 days.

This patent is subject to a terminal disclaimer.

(21) Appl. No.: 17/829,580

(22) Filed: Jun. 1, 2022

(65) Prior Publication Data

US 2022/0287811 A1     Sep. 15, 2022

Related U.S. Application Data

(63) Continuation of application No. 17/066,068, filed on Oct. 8, 2020, now abandoned, which is a continuation (Continued)

(30) Foreign Application Priority Data

Feb. 24, 2016    (DK) ........................... PA 2016-70103

(51) Int. Cl.
*A61C 19/05*          (2006.01)
*A61B 5/11*           (2006.01)
(Continued)

(52) U.S. Cl.
CPC ............. *A61C 19/05* (2013.01); *A61B 5/1111* (2013.01); *A61C 9/0046* (2013.01); *A61C 9/0053* (2013.01); *A61C 19/04* (2013.01)

(58) Field of Classification Search
None
See application file for complete search history.

(56) References Cited

U.S. PATENT DOCUMENTS 4,111,557 A      9/1978   Rottenkolber et al.
5,879,158 A      3/1999   Doyle et al.
(Continued)

FOREIGN PATENT DOCUMENTS

CA          2724654 A1    11/2009
CA          2654854 C      7/2013
(Continued)

OTHER PUBLICATIONS

Extended European Search Report dated Jan. 12, 2021, issued by the European Patent Office in corresponding European Application No. 21175612.7-1122, (8 pages).

(Continued)

*Primary Examiner* — Andrew G Yang
(74) *Attorney, Agent, or Firm* — BUCHANAN INGERSOLL & ROONEY.P.C

(57)          ABSTRACT

A method, user interface and system for detecting and monitoring development of a dental condition. In particular, detecting and monitoring such a development by comparing digital 3D representations of the patient's set of teeth recorded at a first and a second point in time. For example, determining tooth movement for at least one tooth between the first and second point in time based on derived distances.

26 Claims, 5 Drawing Sheets

100

Obtain first digital 3D representation          102

Obtain second digital 3D representation          103

Globally align the first and second digital 3D representations          104

Compare the aligned first and second digital 3D representations          105

Detect a change in a parameter relating to a dental condition based on the comparison between the first and second digital 3D representations          106

Deriving the change in the dental condition from the detected change in the parameter          107

Related U.S. Application Data of application No. 16/079,256, filed as application No. PCT/EP2017/054296 on Feb. 24, 2017, now Pat. No. 10,835,361.

(51) Int. Cl.
  *A61C 9/00* (2006.01)
  *A61C 19/04* (2006.01)

(56) References Cited

U.S. PATENT DOCUMENTS

| | | | |
|---|---|---|---|
| 6,318,994 B1 | 11/2001 | Chishti et al. | |
| 6,350,120 B1 | 2/2002 | Sachdeva et al. | |
| 6,457,972 B1 | 10/2002 | Chishti et al. | |
| 6,463,344 B1 | 10/2002 | Pavlovskaia et al. | |
| 6,602,070 B2 | 8/2003 | Miller et al. | |
| 6,621,491 B1 | 9/2003 | Baumrind et al. | |
| 6,632,089 B2 | 10/2003 | Rubbert et al. | |
| 6,648,640 B2 | 11/2003 | Rubbert et al. | |
| 6,664,986 B1 | 12/2003 | Kopelman et al. | |
| 6,685,470 B2 | 2/2004 | Chishti et al. | |
| 6,711,432 B1 | 3/2004 | Krause et al. | |
| 6,722,880 B2 | 4/2004 | Chishti et al. | |
| 6,739,870 B2 | 5/2004 | Lai et al. | |
| 6,819,318 B1 | 11/2004 | Geng | |
| 6,971,873 B2 | 12/2005 | Sachdeva et al. | |
| 7,013,191 B2 | 3/2006 | Rubbert et al. | |
| 7,027,642 B2 | 4/2006 | Rubbert et al. | |
| 7,077,647 B2 | 7/2006 | Choi et al. | |
| 7,155,373 B2 | 12/2006 | Jordan et al. | |
| 7,156,661 B2 | 1/2007 | Choi et al. | |
| 7,160,110 B2 | 1/2007 | Imgrund et al. | |
| 7,292,716 B2 | 11/2007 | Kim | |
| 7,343,305 B2 | 3/2008 | Benn et al. | |
| 7,347,686 B2 | 3/2008 | Marshall | |
| 7,435,083 B2 | 10/2008 | Chishti et al. | |
| 7,717,708 B2 | 5/2010 | Sachdeva et al. | |
| 8,021,147 B2 | 9/2011 | Sporbert et al. | |
| 8,121,718 B2 | 2/2012 | Rubbert et al. | |
| 8,177,551 B2 | 5/2012 | Sachdeva et al. | |
| 8,416,984 B2 | 4/2013 | Liang et al. | |
| 8,780,106 B2 | 7/2014 | Chishti et al. | |
| 9,158,889 B2 | 10/2015 | Badawi | |
| 10,517,695 B2 | 12/2019 | Van Lierde et al. | |
| 2002/0055800 A1 | 5/2002 | Nikolskiy et al. | |
| 2002/0064759 A1 | 5/2002 | Durbin et al. | |
| 2003/0039389 A1 | 2/2003 | Jones et al. | |
| 2003/0059736 A1 | 3/2003 | Lai et al. | |
| 2003/0105611 A1 | 6/2003 | Sachdeva | |
| 2003/0163291 A1 | 8/2003 | Jordan et al. | |
| 2003/0235803 A1 | 12/2003 | Nikolskiy et al. | |
| 2004/0122306 A1 | 6/2004 | Spoonhower et al. | |
| 2004/0214128 A1 | 10/2004 | Sachdeva et al. | |
| 2004/0224286 A1 | 11/2004 | Kaza et al. | |
| 2005/0048432 A1 | 3/2005 | Choi et al. | |
| 2005/0219242 A1 | 10/2005 | Anh et al. | |
| 2006/0177792 A1* | 8/2006 | Touchstone | A61C 19/04 |
| | | | 433/223 |
| 2007/0105069 A1* | 5/2007 | Yamagishi | A61B 5/0088 |
| | | | 433/29 |
| 2007/0293755 A1* | 12/2007 | Shirahata | A61B 6/463 |
| | | | 600/425 |
| 2008/0124681 A1 | 5/2008 | Cha | |
| 2008/0153067 A1 | 6/2008 | Berckmans et al. | |
| 2010/0208967 A1* | 8/2010 | Wilson | G06T 7/0016 |
| | | | 382/131 |
| 2010/0260405 A1 | 10/2010 | Cinader | |
| 2010/0324875 A1 | 12/2010 | Kalili | |
| 2011/0054308 A1 | 3/2011 | Cohen et al. | |
| 2011/0110575 A1* | 5/2011 | Banumathi | G06T 7/0012 |
| | | | 382/128 |
| 2012/0249551 A1 | 10/2012 | Chernoff et al. | |
| 2013/0044932 A1 | 2/2013 | Caligor et al. | |
| 2013/0058547 A1 | 3/2013 | Kuo et al. | |
| 2014/0172375 A1 | 6/2014 | Grove et al. | |

| | | | |
|---|---|---|---|
| 2014/0358497 A1 | 12/2014 | Kuo et al. | |
| 2015/0025855 A1 | 1/2015 | Fisker et al. | |
| 2015/0305830 A1 | 10/2015 | Howard et al. | |
| 2015/0320320 A1 | 11/2015 | Kopelman et al. | |
| 2015/0348320 A1 | 12/2015 | Pesach et al. | |
| 2015/0359615 A1 | 12/2015 | Sabina et al. | |
| 2016/0004811 A1 | 1/2016 | Somasundaram et al. | |
| 2016/0135925 A1 | 5/2016 | Mason et al. | |
| 2016/0220200 A1 | 8/2016 | Sandholm et al. | |
| 2016/0225151 A1* | 8/2016 | Cocco | G06F 16/51 |
| 2016/0307323 A1* | 10/2016 | Wu | G06T 7/33 |
| 2017/0236327 A1* | 8/2017 | Somasundaram | G06T 19/20 |
| | | | 345/419 |
| 2018/0325631 A1 | 11/2018 | Christiansen et al. | |
| 2019/0060042 A1 | 2/2019 | Fisker et al. | |
| 2021/0045859 A1 | 2/2021 | Fisker et al. | |
| 2021/0161365 A1* | 6/2021 | Kim | A61B 5/0088 |

FOREIGN PATENT DOCUMENTS

| | | | |
|---|---|---|---|
| EP | 0373077 B1 | 3/1996 | |
| EP | 3050534 A1 | 8/2016 | |
| JP | 2002526155 A | 8/2002 | |
| JP | 2011507613 A | 3/2011 | |
| KR | 101517464 B1 | 5/2015 | |
| WO | 0069358 A1 | 11/2000 | |
| WO | 0180765 A1 | 11/2001 | |
| WO | 2009085752 A2 | 7/2009 | |
| WO | 2012008960 A1 | 1/2012 | |
| WO | 2012083960 A1 | 6/2012 | |

OTHER PUBLICATIONS

Office Action (Notice of Reasons for Rejection) issued on Jan. 4, 2021, by the Japanese Patent Office in corresponding Japanese Patent Application No. 2018-544318, and an English Translation of the Office Action. (13 pages).

Office Action {First Office Action) issued on Jul. 28, 2020, by the Chinese Patent Office in corresponding Chinese Patent Application No. 2017800253628, and an English Translation of the Office Action. (10 pages).

Alcaniz, et al., "An Advanced System for the Simulation and Planning of Orthodontic Treatment", Medical Image Analysis, vol. 2, No. 1, 1998, pp. 61-77.

Alcaniz, et al., "An Advanced System for the Simulation and Planning of Orthodontic Treatments", VBC '96: Proceedings of the 4th International Conference on Visualization in Biomedical Computing, 1996, pp. 511-520.

Aoki, et al., "Simulation of Postoperative 3D Facial Morphology Using Physics-Based Head Model", International Archives of Photogrammetry and Remote Sensing. vol. 33, Supplement B5, 2000, pp. 12-19.

Ashmore, et al., "A 3-Dimensional Analysis of Molar Movement During Headgear Treatment", American Journal of Orthodontics and Dentofacial Orthopedics, vol. 121, No. 1, 2002, pp. 18-30.

Bernardini, et al., "High-Quality Texture Reconstruction from Multiple Scans", IEEE Transactions on Visualization and Computer Graphics, vol. 7, No. 4, Oct.-Dec. 2001, pp. 318-332.

Bernardini, et al., "The 3D Model Acquisition Pipeline", Computer Graphics Forum, vol. 21, No. 2, 2002, pp. 149-172.

Besl, et al., "A Method for Registration of 3-D Shapes", IEEE Transactions on Pattern Analysis and Machine Intelligence, vol. 14, No. 2, Feb. 1992, pp. 239-256.

Boyd, et al., "The Invisalign System in Adult Orthodontics: Mild Crowding and Space Closure Cases", Journal of Clinical Orthodontics, vol. 34, No. 4, Apr. 2000, pp. 203-212.

Boyd, et al., "Three-Dimensional Diagnosis and Orthodontic Treatment of Complex Malocclusions With the Invisalign Appliance", Seminars in Orthodontics, vol. 7, No. 4, Dec. 2001, pp. 274-293.

Chuah, et al., "3D Space Analysis of Dental Models", Visualization, Display, and Image-Guided Procedures, Proceedings of SPIE, vol. 4319, 2001, pp. 564-573.

Commer, et al., "Construction and Testing of a Computer-Based Intraoral Laser Scanner for Determining Tooth Positions", Medical Engineering & Physics, vol. 22, 2000, pp. 625-635.

(56) References Cited

OTHER PUBLICATIONS

EP 17 707 016.6-1126 , "Office Action (Communication pursuant to Article 94(3) EPC)", 5 pages.

EP 17707016.6-1126, "Office Action (Communication pursuant to Article 94(3) EPC", 6 pages.

Fiorelli, et al., "The Design of Custom Orthodontic Mechanics", Clinical Orthodontics and Research, vol. 3, 2000, pp. 210-219.

Firelli, et al., "The "3-D Occlusogram" Software", American Journal of Orthodontics and Dentofacial Orthopedics, vol. 116, No. 3, Sep. 1999, pp. 363-368.

Fuhrmann, et al., "Treatment Prediction With Three-Dimensional Computer Tomographic Skull Models", American Journal of Orthodontics and Dentofacial Orthopedics, vol. 106, No. 2, 1994, pp. 156-160.

Furukawa, et al., "A 3D Integration System for Computed Simulation of Orthognathic Surgery", Japanese Journal of Jaw Deformities, vol. 10, No. 3, Dec. 2000, pp. 281-289.

Gold, et al., "New Algorithms for 2D and 3D Point Matching: Pose Estimation and Correspondence", Pattern Recognition, vol. 31, No. 8, 1998, pp. 1019-1031.

Hans, et al., "Three-Dimensional Imaging: The Case Western Reserve University Method" , Seminars in Orthodontics, vol. 7, No. 4, Dec. 2001, pp. 233-243.

Hayashi, et al., "A Novel Method for the Three-Dimensional (3-D) Analysis of Orthodontic Tooth Movement—Calculation of Rotation About and Translation Along the Finite Helical Axis" Journal of Biomechanics, vol. 35, 2002, pp. 45-51.

Huang, et al., "Localization and Comparison of Two Free-Form Surfaces" , Computer-Aided Design, vol. 28, No. 12, 1996, pp. 1017-1022.

Huber, "Automatic Three-Dimensional Modeling from Reality", PhD Thesis, Technical Report, CMU-RI-TR-02-35, Robotics Institute, Carnegie Mellon University, Jul. 23, 2002, 203 pages.

Ip, et al., "Using Shape Distributions to Compare Solid Models", SMA '02: Proceedings of the Seventh ACM Symposium on Solid Modeling and Applications, Jun. 17-21, 2002, 8 pages.

Jiang, et al., "A New Approach to 3D Registration of Multimodality Medical Images by Surface Matching", SPIE vol. 1808, Visualization in Biomedical Computing, 1992, pp. 196-213.

Office Action (Notice of Reasons for Rejection) issued on Mar. 2, 2021, by the Japanese Patent Office in corresponding Japanese Patent Application No. 2018-544318, and an English Translation of the Office Action. (8 pages).

Koch, et al., "A Framework for Facial Surgery Simulation", ETH Zurich, CS Technical Report #326, Institute of Scientific Computing, Jun. 18, 1999, 15 pages.

Koch, et al., "A Framework for Facial Surgery Simulation", SCCG '02: Proceedings of the 18th Spring Conference on Computer Graphics, 2002, pp. 33-42.

Kondo, et al., "Robust Arch Detection and Tooth Segmentation in 3D Images of Dental Plaster Models", Proceedings of the International Workshop on Medical Imaging and Augmented Reality (MIAR'01), 2001, 6 pages.

Krinidis, et al., "3D Volume Reconstruction by Serially Acquired 2D Slices Using a Distance Transform-Based Global Cost Function", I. P. Vlahavas and C. D. Spyropoulos, (Editors), SETN 2002, LNAI 2308, 2002, pp. 390-400.

Leenders, et al., "Reduction in Variability of Acetabular Cup Abduction Using Computer Assisted Surgery: A Prospective and Randomized Study", Computer Aided Surgery, vol. 7, 2002, pp. 99-106.

Mok, et al., "Pose Estimation of Teeth Through Crown-Shape Matching", Medical Imaging 2002: Image Processing, Proceedings of SPIE vol. 4684, 2002, pp. 955-964.

Mokhtari, et al., "Feature Detection on 3-D Images of Dental Imprints", Proceedings of IEEE Workshop on Biomedical Image Analysis, 1994, pp. 287-296.

Monserrat, et al., "Advanced System for 3D Dental Anatomy Reconstruction and 3D Tooth Movement Simulation During Orthodontic Treatment", SPIE, vol. 3031, 1997, pp. 62-72.

Motohashi, et al., "A 3D Computer-Aided Design System Applied to Diagnosis and Treatment Planning in Orthodontics And Orthognathic Surgery", European Journal of Orthodontics, vol. 21, 1999, pp. 263-274.

Myszkowski, et al., "Computer Modeling for the Occlusal Surface of Teeth", Proceedings of CG International '96, 1996, pp. 191-198.

O'Toole, et al., "Three-Dimensional Shape and Two-Dimensional Surface Reflectance Contributions to Face Recognition: An Application of Three-Dimensional Morphing", Vision Research, vol. 39, 1999, pp. 3145-3155.

Okumura, et al., "Three-Dimensional Virtual Imaging of Facial Skeleton and Dental Morphologic Condition for Treatment Planning in Orthognathic Surgery", American Journal of Orthodontics and Dentofacial Orthopedics, vol. 116, No. 2, 1999, pp. 126-131.

Osada, et al., "Matching 3D Models with Shape Distributions", Proceedings International Conference on Shape Modeling and Applications, 2001, 14 pages.

PCT/EP2017/054296, "International Preliminary Report on Patentability received".

PCT/EP2017/054296, "International Search Report received".

PCT/EP2017/054296, "Written Opinion of the International Searching Authority", 5 pages.

Pedersini, et al., "Combined Surface Interpolation and Object Segmentation for Automatic 3-D Scene Reconstruction", Proceedings 1998 International Conference on Image Processing, ICIP98, 1998, pp. 963-966.

Rangarajan, et al., "A Robust Point Matching Algorithm for Autoradiograph Alignment", Medical Image Analysis, vol. 1, 1997, 29 pages.

Romdhani, et al., "Face Identification by Fitting a 3D Morphable Model using Linear Shape and Texture Error Functions", European Conference on Computer Vision, 2002, pp. 1-15.

Rusinkiewicz, et al., "Real-Time 3D Model Acquisition", ACM Transactions on Graphics, vol. 21, 2002, pp. 438-446.

Ryden, et al., "Tooth Position Measurements on Dental Casts Using Holographic Images", American Journal of Orthodontics, vol. 81, No. 4, Apr. 1982, pp. 310-313.

Sachdeva, et al., "JCO Interviews : Dr. Rohit C.L. Sachdeva on A Total Orthodontic Care Solution Enabled by Breakthrough Technology", Journal of Clinical Orthodontics, vol. 34, No. 4, Apr. 2000, pp. 223-232.

Sachdeva, "SureSmile Technology in a Patient-Centered Orthodontic Practice", Journal of Clinical Orthodontics, vol. 35, No. 4, Apr. 2001, pp. 245-253.

Schutz, et al., "Multi-Feature Matching Algorithm for Free-Form 3D Surface Registration", Proceedings 14th International Conference on Pattern Recognition (ICPR), vol. 2, 1998, pp. 982-984.

Thirion, "Image Matching as a Diffusion Process: An Analogy With Maxwell's Demons", Medical Image Analysis, vol. 2, No. 3, 1998, pp. 243-260.

Troulis, et al., "Development of a Three-Dimensional Treatment Planning System Based on Computed Tomographic Data", International Journal of Oral and Maxillofacial Surgery, vol. 31 , 2002, pp. 349-357.

Yamamoto, et al., "Measurements of Dental Cast Profile and Three-Dimensional Tooth Movement During Orthodontic Treatment", IEEE Transactions on Biomedical Engineering, vol. 38, No. 4, Apr. 1991, pp. 360-365

Office Action (Notice of Reasons for Rejection) issued on Oct. 11, 2022, by the Japanese Patent Office in corresponding Japanese Patent Application No. 2018-544318, and an English Translation of the Office Action. (9 pages).

Office Action (Notice to File a Response) issued on Dec. 18, 2023, by the Korean Patent Office in corresponding Korean Patent Application No. 10-2018-7027945, and an English Translation of the Office Action. (18 pages).

* cited by examiner

100

230

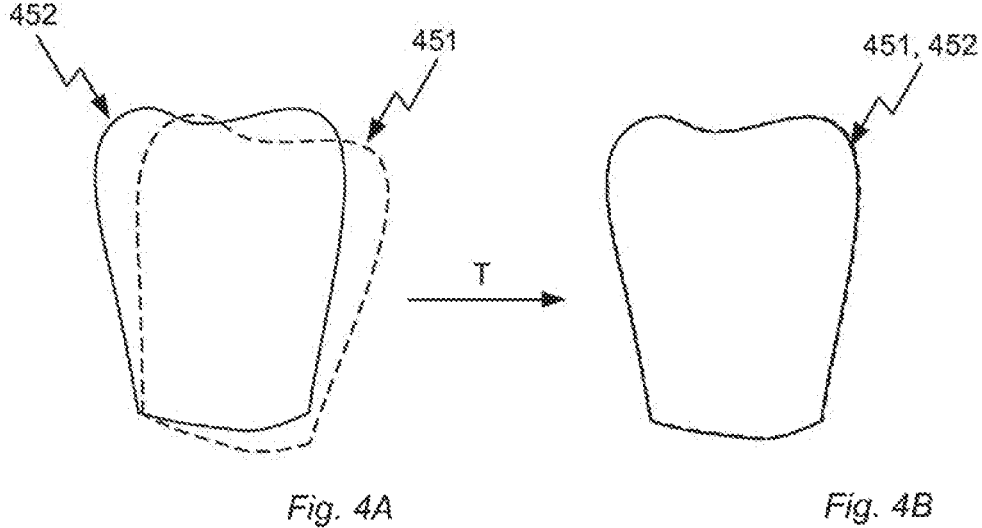
*Fig. 4A*
*Fig. 4B*
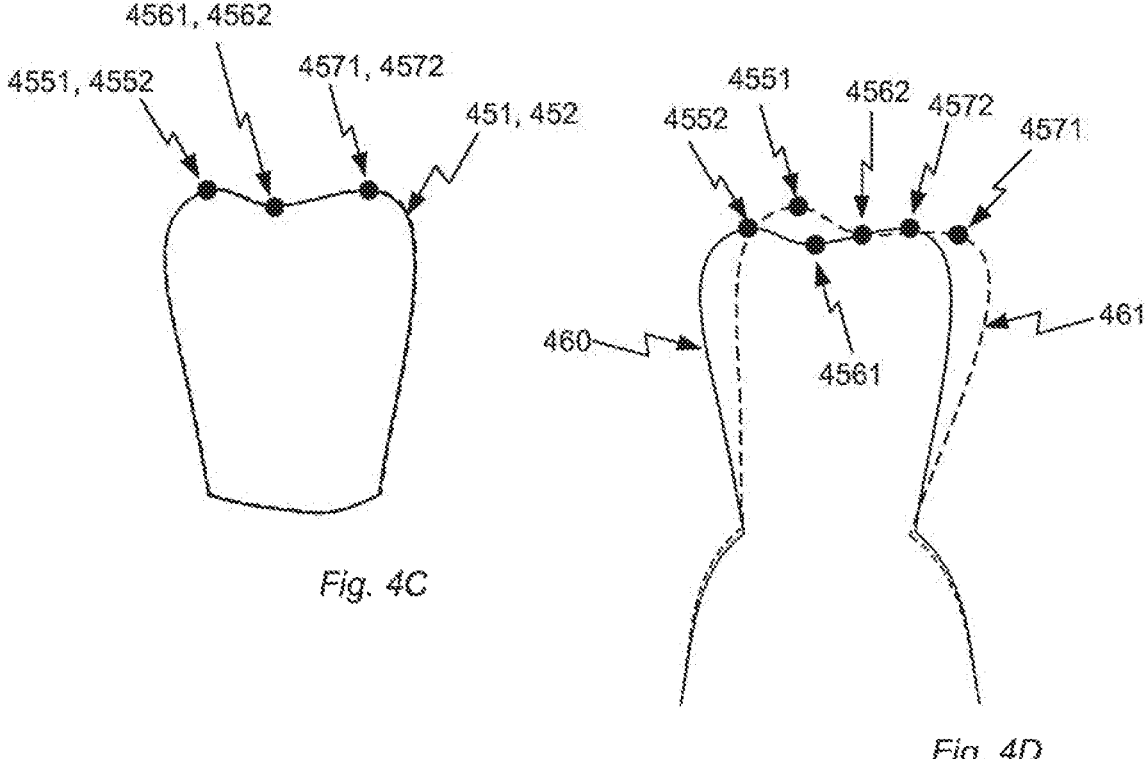
*Fig. 4C*
*Fig. 4D*

DETECTING AND MONITORING DEVELOPMENT OF A DENTAL CONDITION

CROSS REFERENT TO RELATED APPLICATIONS

The present application is a continuation of U.S. application Ser. No. 17/066,068, filed on Oct. 8, 2020, which is a continuation of U.S. application Ser. No. 16/079,256, filed on Aug. 23, 2018, now U.S. Pat. No. 10,835,361, which is a U.S. National Stage of International Application No. PCT/EP2017/054296, filed on Feb. 24, 2017 which claims the benefit of Danish Application No. PA 2016-70103, filed on Feb. 24, 2016. The entire contents of each of U.S. application Ser. No. 16/079,256, International Application No. PCT/EP2017/054296, and Danish Application No. PA 2016-70103 are hereby incorporated herein by reference in their entirety.

TECHNICAL FIELD

This disclosure generally relates to methods, user interfaces, systems, and computer program products for detecting and monitoring development of a dental condition. In particular the disclosure relates to detecting and monitoring such a development by comparing digital 3D representations of the patient's set of teeth recorded at different points in time.

SUMMARY

Disclosed is a method for detecting and monitoring movement of a patient's teeth between a first and a second point in time, wherein the method comprises:

obtaining a first digital 3D representation of the teeth recorded at the first point in time and segmenting the first digital 3D representation such that a first 3D tooth model is formed for at least one tooth;

obtaining a second digital 3D representation of the teeth recorded at the second point in time and segmenting the second digital 3D representation such that a second 3D tooth model is formed for the least one tooth;

locally aligning the first and second 3D tooth models;

selecting one or more corresponding regions on the locally aligned first and second 3D tooth models;

arranging the first and second digital 3D representations or the first and second 3D tooth models according to a global alignment of the patient's set of teeth and deriving the distances between the selected corresponding regions; and determining the tooth movement for the at least one tooth between the first and second point in time based on the derived distances.

Selecting corresponding regions on the locally aligned 3D tooth models provides the advantage that a true geometrical correspondence can be established. Determining tooth movement between different points in time based on the distance between anatomical corresponding regions on the tooth surface provides a more accurate measure than prior art methods which measure distance between closest parts of the tooth surfaces which not necessarily relate to the anatomically identical parts. The anatomical correct distance and movement can, e.g., be determined from a transformation matrix which locally aligns the first and second 3D tooth models.

The detection of the development of, e.g., a tooth movement by comparing two digital 3D representations acquired at different points in time can be extended to comparing several digital 3D representations and to monitor the development of the patient's teeth over time. The monitoring may involve several other digital 3D representations recorded in between, before and/or after the first and second digital 3D representations such that a series of digital 3D representations is recorded.

The comparison can then, e.g., be between two subsequently acquired digital 3D representations or between the latest acquired digital 3D representation and the first digital 3D representation acquired for the patient. In the first example the development since the last visit at the clinic can be detected. In the second example, an overall development since the beginning of the monitoring is detected. In some cases it may however also be advantageous to allow the operator to decide which of the previous digital 3D representations a given digital 3D representation should be compared with. In some embodiments, the user interface configured for implementing the disclosed method provides that the operator can decide which of several obtained digital 3D representations should be compared.

When visualizing the development of the patient's set of teeth based on digital 3D representations recorded at two or more visits to the clinic, the user interface may be configured to visualize the development by aligning all the digital 3D representations and controlling the transparency of the different digital 3D representations based on a timeline indicator. The transparency of a given digital 3D representation then increases when the timeline indicator is positioned away from the corresponding point in time. In that case, preferably only the closest one or two digital 3D representations can be seen for any given indicator position on the timeline.

The digital 3D representations may be obtained using different scanning techniques know to the skilled person, such as an intra oral scanner configured for recording the topography of the patient's set of teeth, i.e. the shape of the gingiva and/or the shape of the individual teeth and their relative arrangement in the mouth.

In some embodiments, the digital 3D representations further comprise texture data, such as color and/or shade data. This may, e.g., be the case when the teeth were scanned using an intra oral scanner capable of recording tooth colors. This provides that changes in the color and/or shade of the teeth can be detected and monitored. Accordingly in some embodiments the detecting comprises determining a color value for at least a region of interest in the first and second digital 3D representation and determining the change in the color value between the first and second digital 3D representation.

In the context of the present invention the phrase "a patient's set of teeth" may refer to the patient's gingiva and/or some or all of the teeth.

In some embodiments, the method comprises segmentation of the first and second digital 3D representations. The segmentation identifies the parts of the first and second digital 3D representations which correspond to the different teeth. The segmentation provides that the identified teeth and the gingiva can be separated and treated as independent 3D models of the individual teeth and the gingiva.

In some embodiments, the method comprises a globally aligning the first and second digital 3D representations. This is advantageous, e.g., when the method is for monitoring changes in the position of the individual teeth, where a direct comparison between the teeth parts of the globally aligned digital 3D representations can be used to detect any tooth movement over time. The alignment provides that the spatial correspondence between the digital 3D representations is determined.

In some embodiments, the global alignment is based on parts of the digital 3D representations corresponding to parts of the set of teeth which most likely have not changed/moved during the time elapsed between the first and second digital 3D representations where recorded. For instance the rugae in the patient's upper jaw can be used in the global alignment of the digital 3D representations as well as teeth which are not expected to move, such as the patient's molar teeth during an orthodontic treatment correcting the position of the anterior teeth only. The global alignment can, e.g., be based on 3 points defined on corresponding parts of the digital 3D representations, on operator selected areas of the digital 3D representations, or on the teeth of one or more of the quadrants in the patient's set of teeth. When a single tooth is moved, e.g., during an orthodontic treatment the global alignment may also be based on the neighboring teeth. For a series of digital 3D representations the alignment may comprise aligning each digital 3D representation with the previous digital 3D representation in the series, i.e. the closest earlier digital 3D representation. In some cases it may however also be advantageous to allow the operator to decide which of the previous digital 3D representations a given digital 3D representation should be aligned with.

In some embodiments, the method comprises locally aligning segmented teeth of the first and second digital 3D representations. In the context of the present application the phrase "locally aligning segmented teeth" refers to the situation where one or more of the segmented teeth of one digital 3D representation are individually aligned with the corresponding teeth of the other digital 3D representation. The local alignment may be realized by aligning corresponding digital 3D models of the teeth extracted from the digital 3D representations, such as, e.g., aligning digital 3D models of a canine tooth extracted from the digital 3D representations. The 3D models of the segmented teeth of the first digital 3D representation are thus aligned with the corresponding 3D models of the teeth in the second digital 3D representation on a tooth to tooth basis. I.e. the alignment is local on the scale of the individual teeth rather than on the global scale of the entire set of teeth. There transformations used for aligning different segmented teeth may thus be different in contrast to a global alignment where the same transformation is applied to all the teeth and the gingiva.

The local alignment of the 3D models of the segmented teeth provides the advantage that corresponding teeth of the digital 3D representations can be aligned accurately regardless of any relative movement of the teeth in between the recording of the digital 3D representations. A true anatomical correspondence between teeth of the digital 3D representations can thus be obtained.

In some embodiments, selecting one or more corresponding regions on the locally aligned first and second 3D tooth models comprises selecting the entire surface of the first and/or second 3D tooth model. The movement of the tooth is then determined for the entire tooth surface providing a robust determining of the moved distance and that, e.g., a distance map can be device from the globally aligned first and second 3D tooth models or from the globally aligned first and second digital 3D representations. The distance map expressing the variation in the distance over the entire tooth surface.

In some embodiments, the method comprises selecting one or more regions of interest for the patient's set of teeth. The regions of interest can for example be indicated on the first digital 3D representation and the corresponding regions on the second digital 3D representation can then be determined based on the spatial correspondence between the first and second digital 3D representation.

In some embodiments, the method comprises defining one or more watch points for the patient's set of teeth and detecting changes in the parameter between the first and second digital 3D representations at the portions of these located at the watch point. Similar to the regions of interest the watch points may be indicated on the first digital 3D representation and the corresponding parts of the second digital 3D representation can then be determined based on the spatial correspondence between the first and second digital 3D representation.

The regions of interest and/or the watch points can, e.g., be defined for parts of the patient's set of teeth where the dentist expects that some dental condition may be developing. For example the dentist can choose to define a watch point where he or she suspects that color changes on the tooth surface are an early indication of caries development.

Disclosed is a method for detecting development of a dental condition for a patient's set of teeth between a first and a second point in time, wherein the method comprises:
  obtaining a first digital 3D representation of the teeth recorded at the first point in time;
  obtaining a second digital 3D representation of the teeth recorded at the second point in time; and
  comparing at least part of the first and second digital 3D representations.

Disclosed is also a method for monitoring a patient's set of teeth, wherein the method comprises:
  obtaining a series of digital 3D representations of the teeth recorded at different points in time;
  aligning at least part of the digital 3D representations;
  comparing at least part of the aligned digital 3D representations; and
  detecting a development of at least one dental condition of the teeth based on said comparison.

In some embodiments, a change in a parameter relating to the dental condition is detected based on the comparison.

The parameter can relate to different indications for the patient's set of teeth, such as the color, shade, size and shape of one or more teeth, the relative arrangement of the teeth, the health of the gingiva and its position relative to the teeth, the occlusal contacts between the teeth in the upper and lower jaw. The parameter or changes in the parameter over time can provide information relating to the development of one or more dental conditions for the set of teeth. The detected change in the parameter then visualizes and/or quantifies the development of the dental condition between the first and second points in time, i.e. during the elapsed between the recording of the first and second digital 3D representations. For example a reduction in the tooth size can be caused by Bruxism induced tooth wear, such that by following changes in the tooth size the damages caused by the Bruxism are monitored.

When the digital 3D representations of the patient's set of teeth includes data relating to the gingiva different parameters expressing a condition of the gingiva can be determined and changes in the parameters can be detected and monitored by the comparison of the digital 3D representations.

In some embodiments, the dental condition relates to gingival recession at one or more teeth. The development of the gingival recession can then be detected, e.g., from a change in the positon and shape of the gingival boundary at the one or more teeth from the first to the second digital 3D representation.

I.e. the parameter may relate to the positon and/or shape of the gingival boundary at the one or more teeth. Accordingly in some embodiments, the detecting comprises identifying the gingival boundary for said one or more teeth in the first and second digital 3D representation and determining the change in the positon and/or shape of the gingival boundary between the first and second digital 3D representation.

The gingival part of the digital 3D representations can be identified by a segmentation of the set of teeth which isolates the gingival part of the digital 3D representations from the teeth parts. The gingival boundary can also be determined based on texture data of the digital 3D representations. The texture data may comprise color data such that the teeth and gingiva can be distinguished based on their different colors.

In the context of the present application the phrase "gingival boundary" may refer to the gingival margin or the gingival sulcus at a tooth.

A gingival recession can be caused by be various factors, such as a retraction of the gingival margin from crown of teeth, a deliberate removal of gingiva using, e.g., a laser adjusting the gingiva profile to provide for a more aesthetic smile, or gingival release from the teeth surface. The change in the shape and/or position of the gingiva caused by a gingival recession can be quantified in different ways.

When monitoring for a development in a dental condition relating to the patient's gingiva it may be advantageous to base the alignment on the tooth parts of the digital 3D representations and compare larger sections of the digital 3D representations including both the data for the tooth and for a portion of the adjacent gingiva. Since the alignment is based on the segmented teeth it will not be affected by any gingival recession or tooth movement that has occurred between the recordings of the digital 3D representations. Accordingly in some embodiments, the transformation for locally aligning the segmented teeth is applied to at least a section of the digital 3D representations comprising data expressing the shape of the gingiva at the tooth. The gingival boundary is identified in each section and the comparison used for determining the change in the position and/or shape of the gingival boundary is based on the section of the digital 3D representation aligned according to the local transformation. When the sections of the digital 3D representations are aligned any changes in the gingival boundary will become apparent. The precise local alignment of the digital 3D representations in the region near the tooth provides that the detected position of the gingival boundary is very precise and the measure of the gingival recession between the recording of the first and second digital 3D representations is accordingly also very precise.

In some embodiments, the method comprises:
  generating a first and a second 3D model of a tooth by segmentation of the corresponding parts of the first and second digital 3D representations, respectively;
  determining the transformation which aligns first and second 3D tooth models;
  arranging the digital 3D representations according to the determined transformation;
  identifying in each digital 3D representations the gingival boundary at the tooth; and
  detecting a change in the positon of the gingival boundary by comparing the identified gingival boundaries in first and second digital 3D representations arranged according to the determined transformation.

The geometrical correspondence and/or the transformation between the 3D tooth models can, e.g., be expressed in terms of a transformation matrix for locally aligning the segmented teeth.

Disclosed is a method for detecting development in gingival recession at a tooth between a first and a second point in time, wherein the method comprises:
  obtaining a first digital 3D representation of the patient's set of teeth recorded at the first point in time;
  obtaining a second digital 3D representation of the patient's set of teeth recorded at the second point in time;
  generating a first and a second 3D model of the tooth by segmentation of the corresponding parts of the first and second digital 3D representations, respectively;
  determining a local transformation which aligns first and second 3D tooth models;
  arranging the first and second digital 3D representations according to the determined local transformation; and
  detecting a development in the gingival recession between the first and second point in time by comparing the gingival boundaries in the first and second digital 3D representations arranged according to the determined local transformation.

The local transformation may be expressed as a transformation matrix which brings the 3D tooth models into the same coordinate system, such as a transformation matrix which brings the first 3D tooth model into the coordinate system of the second 3D tooth model or vice versa. When the digital 3D representations also are arranged according to the local transformation the tooth portions of the first and second digital 3D representations are aligned with the same precision as the 3D tooth models. This provides the advantage that a change in the position or shape of the gingival boundary easy and precisely can be inferred by comparing the aligned digital 3D representations.

In some embodiments, only sections or regions of interest of the digital 3D representations are aligned according to the transformation. The sections including data for at least part of the gingival boundary and the detection of the gingival recession is then at least partly based on these sections or regions of interest. Using only a section of the digital 3D representations has the advantage that less computer power is required for the different operations.

This approach can also be used when the parameter relates to the color or shape of the gingiva where it provides that the correct portions of the gingiva are compared.

There are further ways for quantifying the gingival recession. For example the distance from the incisal edge/occlusal surface of a tooth to the gingival boundary can be measured in different positions on the tooth surface and the maximum distance provides a measure for the position of the gingival boundary. The development of the gingival recession over time can be quantified by detecting the change in the maximum distance between the first and second digital 3D representations. Assuming little reduction in the height of the teeth (which could be the result of bruxism) the changes in the distance will be dominated by the recession of the gingiva. The tooth equator, i.e. the line where the tooth has its largest circumference, can also be used instead of the incisal edge eliminating any bruxism induced uncertainty.

In some embodiments, the different regions of the gingiva are identified and correlating with the corresponding teeth.

Yet another way is to monitor the change in the area of labial/buccal surfaces of the teeth which is limited by the gingival boundary. I.e. in some embodiments, detecting the change in the gingival boundary comprises determining the labial/buccal areas of the teeth in the first and second digital 3D representations and comparing these areas. An increase in the area from the first to the second digital 3D representation then indicates a recession of the gingiva.

In some embodiments, detecting the change in the gingival boundary comprises determining the area and/or volume of the gingiva in a region of interest at the gingival boundary for the first and second digital 3D representations and comparing the determined areas and/or volumes. A decrease in the area and/or volume in the region of interest can be used to quantify and monitor the gingival recession.

In some embodiments, the parameter relates to the texture of the gingiva, such as the color of the gingiva. Detecting change in the gingival color may then comprise determining a color value for at least a region of interest in the gingival part of the first and second digital 3D representation and determining the difference in the determined color values for the first and second digital 3D representation.

When determined at the gingiva a change in color of the gingiva can be caused by a dental condition such as inflammation, cancer or a stretching of the gingiva making the gingiva whiter.

In some embodiments, the dental condition causes the shape of the gingiva at the alveolar bone to change. Detecting the change may then comprise determining the gingival profile at the alveolar bone in the first and second digital 3D representation and determining the change in the profile. The comparison of the gingiva profiles can be based on an alignment of the gingiva profiles such that variations on a larger scale can be identified. When the height of the gingiva at the alveolar bone, measured, e.g., relative to the surface of the corresponding tooth, is determined for each digital 3D representation this measure can also be used to detect a development.

The smoothness of the gingiva at can also be compared for the two digital 3D representations and used to detect a development of a dental condition.

In some embodiments, the dental condition relates to the health of a patient's gingiva in a region where an implant has been arranged in the patient's jaw bone. The method can then be used for monitoring the healing of the gingiva during osseointegration where a healing abutment often is placed in the implant. The gingiva should preferably adhere to the sides of the healing abutment to be shaped according to the healing abutment once the osseointegration is complete. If the gingiva retracts during osseointegration an alarm should be given since this is a sign that the gingiva is not healing well.

In some embodiments, the dental condition relates to the arrangement of an implant in the patient's jaw bone. The method can then be used for monitoring any changes in the implant position and orientation relative to the patient's jaw bone and existing teeth in the patient's mouth during osseointegration of the implant into the bone.

A healing abutment is often arranged in the implant while the implant integrates into the jaw bone. The healing abutment is firmly attached to the implant during the osseointegration such that any change in the implant position and orientation relative to, e.g., neighboring teeth will result in a corresponding change in the position and orientation of the healing abutment. By aligning a CAD model of the healing abutment with the digital 3D representation the orientation and position of the healing abutment can be determined for each digital 3D representation. When the orientation and position of the healing abutment is known the implant orientation and position of the implant can be derived, e.g., based on a code on the healing abutment providing information relating to, e.g., the size and shape of the healing abutment. Comparing the implant orientation and position for digital 3D representations recorded at different times allows for a detection of changes in the orientation and position during osseointegration. This provides the advantage that the osseointegration can be monitored and, e.g., an alarm can be raised if the orientation and position of the implant changes too much during the osseointegration. In some cases the abutment and crown for the implant are designed when the implant position is planned. In such cases it is also important to monitor the change in the implant orientation and position since a redesign of the abutment and crown may be required.

In some embodiments, the parameter relates to the shape and size of at least one tooth. The development expressed by a change in the parameter can then be that of a gradual reduction of the size or shape at the occlusal surface of at least one tooth. This can, e.g., be used when monitoring the patient's teeth for damages to the occlusal surface of one or more teeth changes due to, e.g., acid induced damages or bruxism where the patient is grinding his teeth.

In some embodiments, the detecting is based on comparing the locally aligned segmented teeth of the first and second digital 3D representations, i.e. the aligned 3D teeth models obtained by the segmentation of the teeth of the first and second digital 3D representations are compared to determine whether the size or shape of at least one tooth has changed. Comparing the individually aligned 3D teeth models has the advantage that any tooth movement between the recording of the first and second digital 3D representations will not interfere with the measurement of the change in tooth size and/or shape.

Disclosed is a method for detecting development of tooth wear caused, e.g., by bruxism or acid damages between a first and a second point in time, wherein the method comprises:

obtaining a first digital 3D representation of the teeth recorded at the first point in time;
    obtaining a second digital 3D representation of the teeth recorded at the second point in time;
    segmentation the first and second digital 3D representations generating a first and a second 3D tooth models for at least one tooth from the first and second digital 3D representations, respectively;
    locally aligning the first and second 3D tooth models;
    comparing the locally aligned first and second 3D tooth models; and
    detecting based on the comparison a change in the tooth size and/or shape.

In some embodiments, the method comprises correlating a detected change in the tooth size with a threshold value relating to an expected depth of the patient's enamel. When the detected change, e.g. the reduction of the tooth height, is above the threshold value an alarm may be given warning the operator that the patient is close to missing enamel in the region of the tooth where the threshold value is exceeded. A detected change in the tooth shape at the occlusal surface may also be correlated with a threshold value and an alarm given when, e.g., the structure on the occlusal surface has diminished significantly.

When the digital 3D representations comprise data expressing the color and/or shade of the teeth, changes in the color and/or shade of the teeth can be detected and monitored over time. Accordingly in some embodiments, the parameter relates to color and/or shade of at least one tooth and the development of the dental condition is detected based on a change in the tooth color and/or shade. A monitoring of changes in the tooth color or tooth shade over time can then be provided by comparing digital 3D representations recorded over time. This provides the advantage that a precise measure for the changes of color or shade can be provided in contrast to the situation where the dentist try to remember how the tooth color and shade was at the last visit.

In some embodiments, the detecting comprises selecting a region of interest and recording a change in color and/or shade value between the first and second digital 3D representation for the region of interest. This is, e.g., advantageous when the dentist has identified a region of interest on the patient's teeth where he wants to evaluate and/or monitor changes in tooth color or shade. In some embodiments, the detected change in the color or shade value is correlated with an expected change in the color or shade in response to the development of caries. The color of a region where caries is developing is known to change to a whiter shade before becoming more brownish. This provides the advantage that the dentist can easily evaluate or monitor whether caries is developing in that particular region.

In some embodiments, the detecting comprises determining the area of a region of a tooth having a color or shade different from the remaining parts of the tooth and recording a in the area from the first to the second digital 3D representation.

In some embodiments, the detected change in the area is correlated with an expected change in response to the development of caries, i.e. an expected increase in the area over time as the caries region grows.

When changes in the tooth color/shade or area of a suspicious region are used to detect the development of caries an alarm signal may be prompted to the operator when the change reaches a threshold value. For a color based detecting this may, e.g., be when the while spot begins to change color to brown.

In some embodiments, wherein the detecting comprises determining a color of shade difference map for first and second digital 3D representations by comparing the shade data or color data of the two digital 3D representations. This provides that any changes in the color over the different parts of the teeth easily can be visualized, e.g., by displaying the difference map on a screen.

In some embodiments, the method is used for monitoring overall changes in the color of a patient's teeth over time, such as for monitoring the darkening of the teeth after a bleaching. The method may also be used for detecting the result of a bleaching treatment by detecting how many steps down the shade ladder the bleaching treatment has resulted in.

In some embodiments, the dental condition parameter relates to the position and/or area of one or more antagonist contact points over the tooth surfaces. When the patient bites the opposing teeth of the upper and lower jaw contacts each other, e.g., on the occlusal surfaces of the molar teeth. The distribution and size of the contact points may change over time, e.g., because of Bruxism induced wear of the occlusal surfaces or in response to a gradual change in the patient's jaw movement in a bite. When there's change in the patient's bite function the area of a contact point can decrease and in severe cases the contact point may eventually disappear. If this is detected in due time a treatment can be initiated in due time to avoid bite function problems. Accordingly in some embodiments, the derived change relates to changes in the position or area of one or more of the antagonist contact points.

This derived change in the area can then be correlated with a minimum area, while the displacement of a contact point on the occlusal surface can be correlated with a maximum displacement. When either threshold (i.e. the minimum area or the maximum displacement) is reached action should be taken and an alarm is given.

Disclosed is a method for detecting tooth wear or change in the patient's bite function between a first and a second point in time, wherein the method comprises:
  obtaining a first digital 3D representation of the teeth recorded at the first point in time;
  obtaining a second digital 3D representation of the teeth recorded at the second point in time;
  segmentation of the teeth in the first and second digital 3D representations;
  locally aligning the segmented teeth;
  detecting one or more antagonist contact points for at least one of the segmented teeth;
  comparing the position and/or areas of the contact points for the first and second digital 3D representations; and
  detecting based on the comparison tooth wear and/or changes in the patient's bite function.

In some embodiments, the method comprises generating a graph showing the derived change in the parameter over time. The graph may, e.g., represent the change in the tooth size in response to Bruxism, the changes in the position of the gingival boundary in response to gingival retraction, change in color/shade values of the teeth or gingiva, etc. over time.

The present invention relates to different aspects including the method, system, user interface, and computer program product described above and in the following, and corresponding methods, systems, user interfaces, and computer program product, each yielding one or more of the benefits and advantages described in connection with the first mentioned aspect, and each having one or more embodiments corresponding to the embodiments described in connection with the first mentioned aspect and/or disclosed in the appended claims.

Disclosed is a user interface for deriving, evaluating, monitoring or visualizing a change in a condition of a patient's set of teeth, wherein the user interface is configured for:
  obtaining a first digital 3D representation of the teeth recorded at a first point in time;
  obtaining a second digital 3D representation of the teeth recorded at a second point in time;
  comparing at least parts of the first and second digital 3D representations; and
  detecting based on the comparison a change in a parameter relating to the dental condition.

Furthermore, the invention relates to a computer program product comprising program code means for causing a data processing system to perform the method according to any of the embodiments when said program code means are executed on the data processing system.

Disclosed is a non-transitory computer readable medium encoded with a computer program product providing a graphical user interface for deriving, evaluating, monitoring or visualizing a change in a condition of a patient's set of teeth by a method comprising:
  obtaining a first digital 3D representation of the teeth recorded at a first point in time;
  obtaining a second digital 3D representation of the teeth recorded at a second point in time;
  comparing at least parts of the first and second digital 3D representations; and detecting based on the comparison a change in a parameter relating to the dental condition.

Disclosed is a computer program product for deriving, evaluating, monitoring or visualizing a change in a condition of a patient's set of teeth, wherein the computer program product is configured for:

obtaining a first digital 3D representation of the teeth recorded at a first point in time;

obtaining a second digital 3D representation of the teeth recorded at a second point in time;

comparing at least parts of the first and second digital 3D representations; and detecting based on the comparison a change in a parameter relating to the dental condition.

Disclosed is a system for deriving, evaluating, monitoring or visualizing a change in a condition of a patient's set of teeth, wherein the system comprises a data processing unit and a non-transitory computer readable medium encoded with a computer program product providing a digital tool for deriving, evaluating, monitoring or visualizing the change by a method comprising:

obtaining a first digital 3D representation of the teeth recorded at a first point in time;

obtaining a second digital 3D representation of the teeth recorded at a second point in time;

comparing at least parts of the first and second digital 3D representations; and detecting based on the comparison a change in a parameter relating to the dental condition.

Disclosed is a system for deriving, evaluating, monitoring or visualizing a change in a condition of a patient's set of teeth, wherein the system comprises a data processing unit and a non-transitory computer readable medium encoded with a computer program product providing a digital tool for deriving, evaluating, monitoring or visualizing the change, wherein the system is configured for loading a first digital 3D representation of the teeth recorded at a first point in time and a second digital 3D representation of the teeth recorded at a second point in time into the computer readable medium, and where the computer program product is configured for comparing at least parts of the first and second digital 3D representations and detecting based on the comparison a change in a parameter relating to the dental condition when program code of the computer program product are executed on the data processing unit.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIGS. 4A-4D illustrate how anatomically correct measurement of tooth movement can be made.

DETAILED DESCRIPTION

In the following description, reference is made to the accompanying figures, which show by way of illustration how the invention may be practiced.

Figure 1:
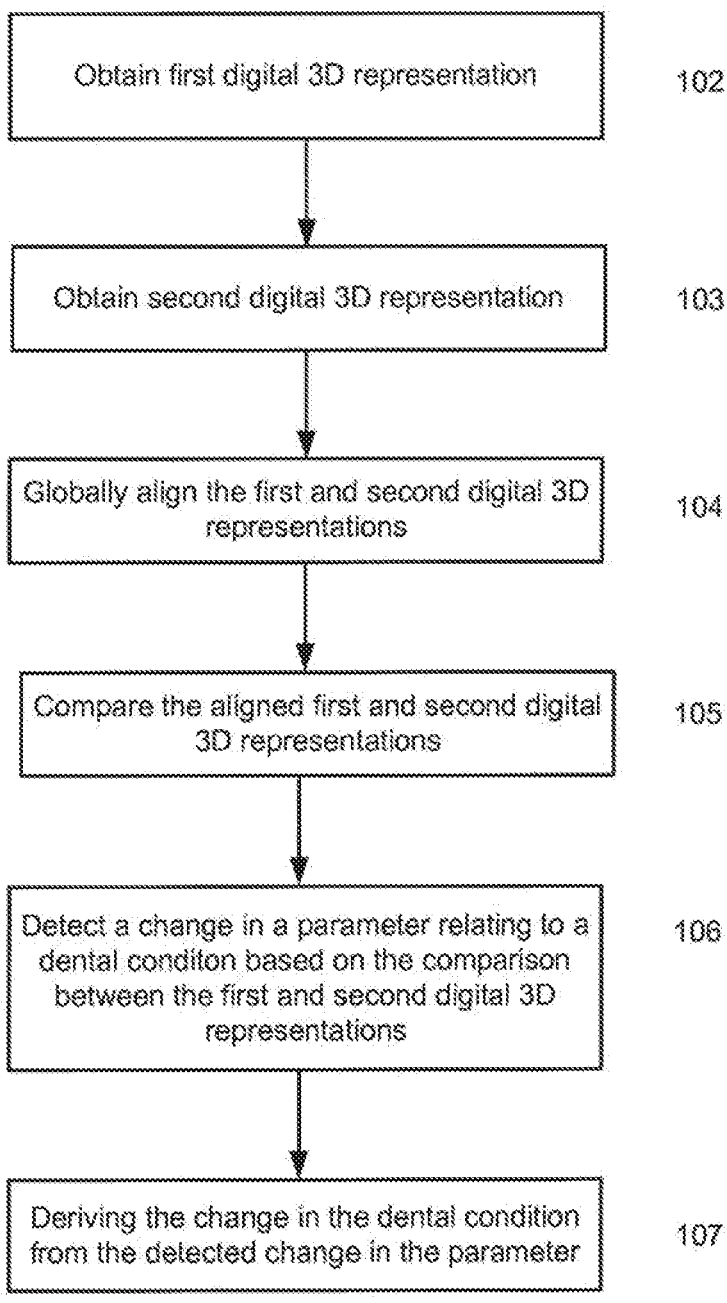
FIG. 1 shows a workflow for an embodiment.

FIG. 1 shows a workflow for an embodiment of the method for detecting development of a dental condition for a patient's set of teeth between a first and a second point in time. The workflow 100 includes steps 102, 103 for obtaining a first and a second digital 3D representation of the patient's set of teeth. The digital 3D representations can be recorded using an intra oral scanner, such as the TRIOS 3 intra oral scanner by 3shape A/S which can record both the topography and color of the patient's set of teeth. The recorded digital 3D representations then expresses both the geometry and colors of the scanned teeth at the first and second points in time. Color calibrating the scanner regularly or just prior to the scanning provides that the measured colors are true and that the color recorded at one visit at the dentist can be compared with the colors measured at another visit.

In step 104 the first and second digital 3D representations are globally aligned using, e.g., a 3-point alignment where 3 corresponding regions are marked on the first and second digital 3D representations. The aligned digital 3D representations can then be visualized in the same user interface and comparisons between shapes and sizes of teeth can be made straightforward. The global alignment of the digital 3D representations can be performed using a computer implemented algorithm, such as an Iterative Closest Point (ICP) algorithm, employed to minimize the difference between digital 3D representations.

In step 105 the aligned first and second digital 3D representations are compared, e.g., by calculating a difference map showing the distance between the digital 3D representations at the different parts of the teeth of teeth. Such as difference map can, e.g., be used for monitoring tooth movement during an orthodontic treatment. Based on the comparison a change in a parameter relating to the dental condition can be detected in step 106 and the change in the parameter can be correlated with a development of a dental condition in step 107.

When the dental condition corresponds to caries and the development of the caries is monitored using change in tooth color from white to brown in the infected region, the global alignment and comparison of the digital 3D representations provide that a change in the tooth color to a more brownish color in a region of the teeth can be detected and the region can be visualized to the operator. The change in the color can be measured using color values of, e.g., the RGB system and can be correlated with knowledge of the usual changes in tooth colors during development of caries.

Figure 2A:
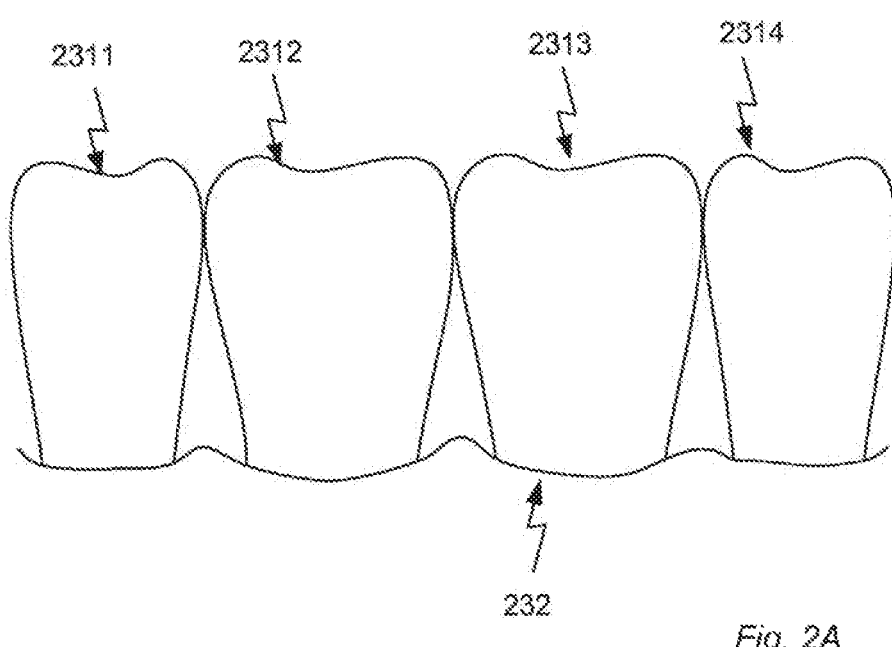
FIGS. 2A-2B show a set of teeth and segmentation of a tooth.
Figure 2B:
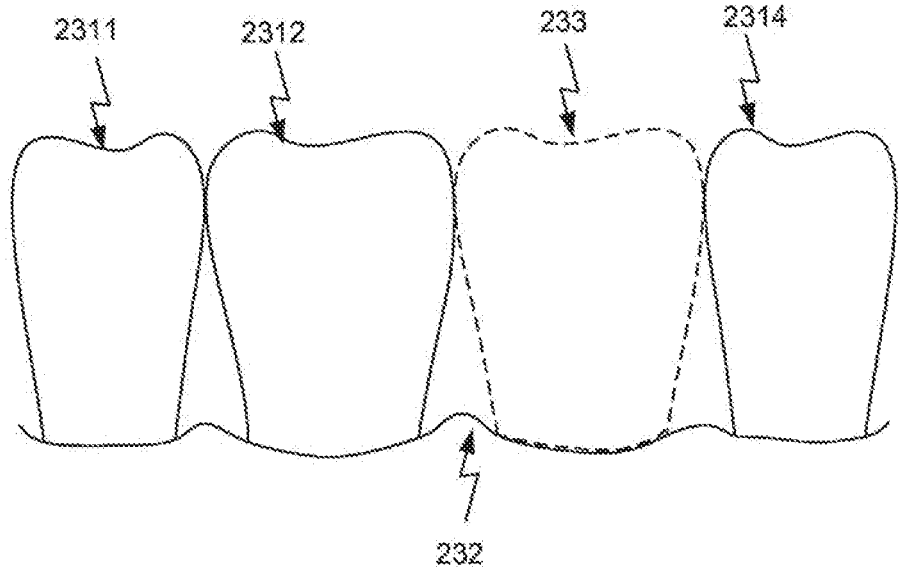

FIGS. 2A-2B show a digital 3D representation of a set of teeth and segmentation of the digital 3D representation to create a 3D model of a tooth. The digital 3D representation 230 has topography data for four anterior teeth 2311, 2312, 2313, 2314 and for a portion of the corresponding gingiva with the gingival boundary 232 as indicated in FIG. 2A. The segmentation of the digital 3D representation provides a 3D tooth model 233 which has the shape of the corresponding tooth part of the digital 3D representation 2312 and is bounded by the gingival boundary 232. In FIG. 2B the 3D tooth model 233 is still arranged along with the other parts of the digital 3D representation according to the arrangement of the tooth in the digital 3D representation.

Figures 3A, 3B, 3C:
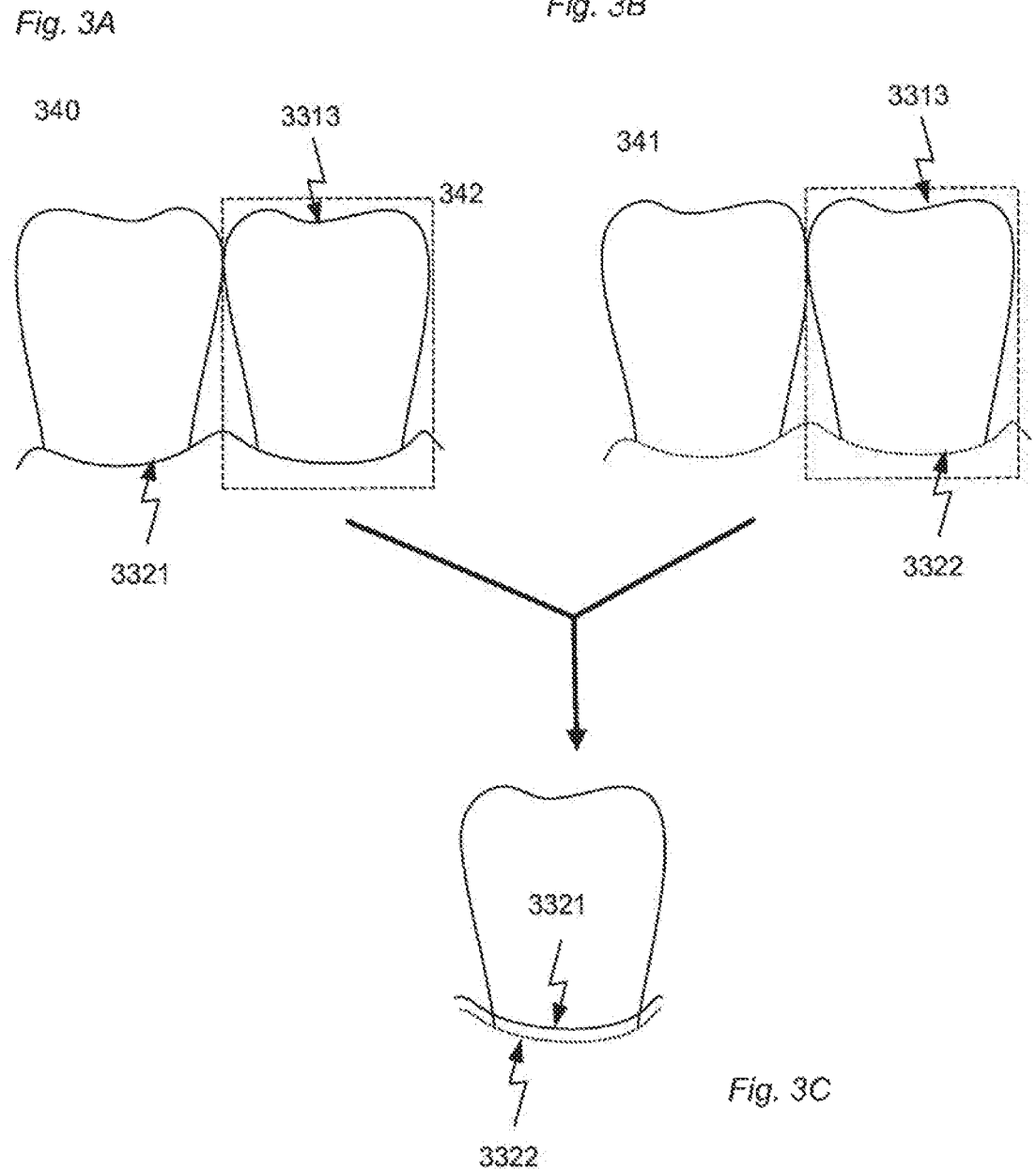
FIGS. 3A-3C illustrate an embodiment for detecting gingival retraction.

FIGS. 3A-3C illustrates an embodiment for detecting gingival retraction at the patient's left central incisor 3313. This tooth is segmented in both the first 340 and second 341 digital 3D representation of the set of teeth showing the two central incisors in the lower jaw and the gingival boundary 332 as seen inn FIGS. 3A and 3B. The change in the position of the gingival boundary is so small that when the two digital 3D representations are seen separately the change is hardly visible. A section having topography data relating to both the tooth surface and the gingiva is selected and the two sections are locally aligned based on the tooth topography data. The local alignment can be performed using iterative closest point algorithm. All data of the sections are aligned according to this local transformation as seen in FIG. 3C and the gingival retraction from the boundary 3321 in the first digital 3D representation to the 3322 boundary in the second digital 3D representation becomes clearly visible. The gingival retraction can now be measured as the distance between the two boundaries.

FIG. 4A shows cross sections of a first 3D tooth model 451 and a second 3D tooth model 451 segmented from a first and a second digital 3D representation, respectively. The first digital 3D representation can for example represent the patient's teeth at the onset of an orthodontic treatment and the second digital 3D representation at some point during the treatment. A transformation T which aligns the first 3D tooth model with the second 3D tooth model is determined and applied to the first 3D tooth model to provide that the two tooth models are locally aligned as illustrated in FIG. 4B. In FIG. 4C three portions 4551, 4561 and 4571 are selected on the first 3D tooth model 451. Since the first and second 3D tooth models are locally aligned the anatomically corresponding portions 4552, 4562 and 4572 can readily and precisely be identified on the second 3D tooth model 451. In FIG. 4D portions 4551, 4561 and 4571 are marked on corresponding portions of the first digital 3D representation 460 and portions 4552, 4562 and 4572 are marked on the corresponding portions of the second digital 3D representation 461. The first and second digital 3D representations are global aligned based, e.g., on the other teeth of the same quadrant or same arch. The anatomical correct distance between the marked regions can then be determined and based on these distances a measure for the movement of the tooth between the first and second point in time can be derived.

In short the workflow described here has the following steps:

selecting one or more corresponding regions on the locally aligned segmented teeth, globally aligning the first and second digital 3D representations;

identifying the selected corresponding regions on the globally aligned first and second digital 3D representations deriving the distances between the selected corresponding regions on the globally aligned first and second digital 3D representations determining the tooth movement based on the derived distances.

In a computer program product configured for implementing the method the portions on the first 3D tooth model can be selected by an operator or by the computer program product when this is configured for detecting appropriate portions, such as characteristic portions on the cusp. The selected portion can also be the entire tooth surface such that a distance map is derived showing the movement for the entire surface.

Other workflows can also be used to measure the distance such as:

selecting one or more corresponding regions on the locally aligned segmented teeth, arranging the first and second 3D tooth models according to the global alignment;

deriving the distances between the selected corresponding regions in the global alignment of the first and second 3D tooth models;

determining the tooth movement based on the derived distances.

Figure 5:
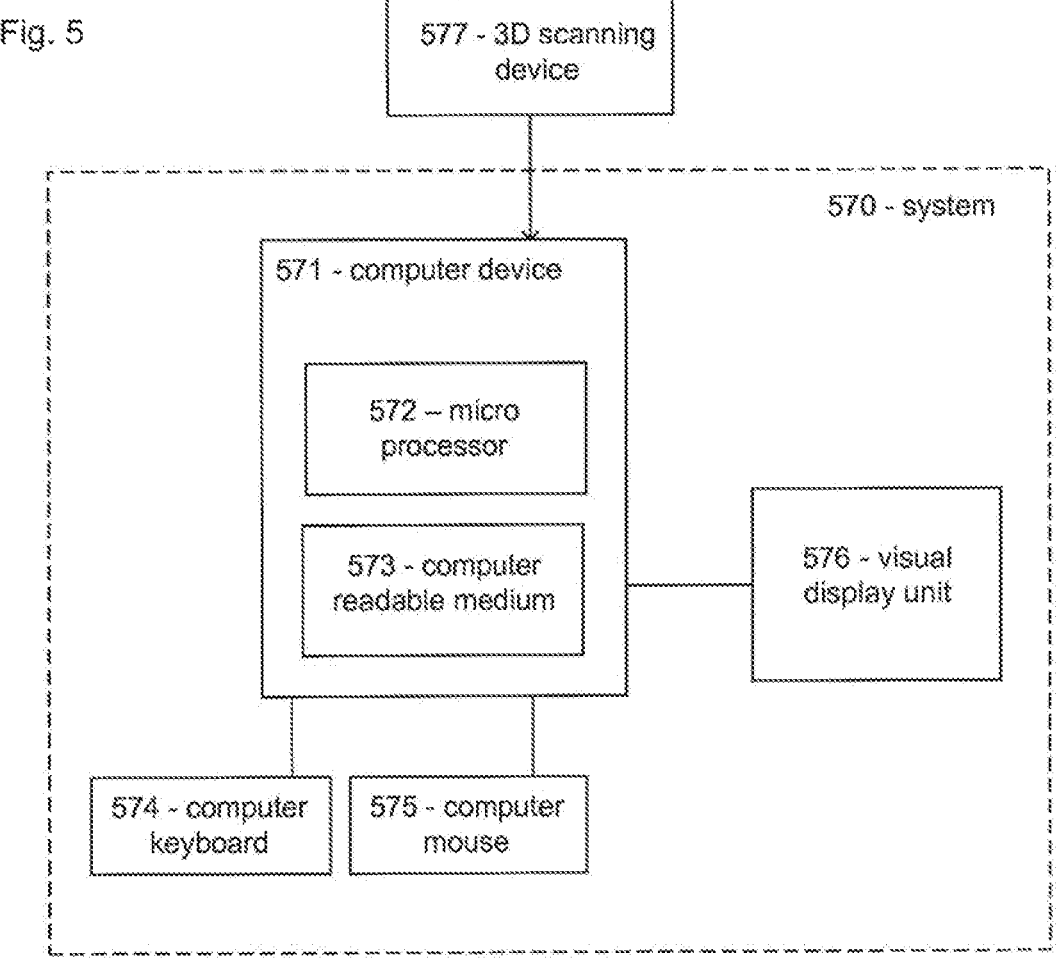
FIG. 5 shows an outline of a system.

FIG. 5 shows a schematic of a system according to an embodiment. The system 570 has a computer device 571 with a data processing unit in the form of a microprocessor 572 and a non-transitory computer readable medium 573 encoded with a computer program product providing a digital tool for determining the movement of teeth, e.g., during an orthodontic treatment. The system further has a visual display unit 576, a computer keyboard 574 and a computer mouse 575 for entering data and activating virtual buttons of a user interface visualized on the visual display unit 576. The visual display unit 576 can, e.g., be a computer screen. The computer device 571 is capable of storing obtained digital 3D representations of the patient's teeth in the computer readable medium 573 and loading these into the microprocessor 572 for processing. The digital 3D representations can be obtained from a 3D color scanner 577, such as the 3Shape TRIOS 3 intra-oral scanner, which is capable of recording a digital 3D representation containing both geometrical data and color data for the teeth.

Besides color and geometry data the digital 3D representation can also include diagnostic data, such fluorescence data obtained using an intra-oral scanner.

The computer readable medium 573 can further store computer implemented algorithms for segmenting a digital 3D representation to create digital 3D models of the individual teeth and for selecting regions on the surface for a local alignment. When digital 3D models for the same tooth is created from different digital 3D representations, such as digital 3D representations recorded at different points in time, the digital 3D models can be locally aligned using, e.g., Iterative Closest Point algorithms (ICP) for minimizing the distance between the surfaces of the digital 3D representations. The digital 3D representations of the patient's entire set of teeth or sections thereof can be globally aligned also using such ICP algorithms. When the digital 3D representations of the teeth are globally aligned with the anatomically correct corresponding regions of a given tooth identified by the local alignment procedure applied to the digital 3D model of that tooth, the precise measure of the movement of the tooth between the points in time where the two digital 3D representations were recorded can be determined.

When the tooth movement has been determined it can be visualized to the operator in the visual display unit 576, e.g., as a distance map or using a cross sectional view of the 3D tooth models or the digital 3D representations.

The digital 3D models of the individual teeth can be stored on the computer readable medium and be re-used at the next visit for the identification of individual teeth in a digital 3D representation recorded at the next visit.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention claimed is:

1. A non-transitory computer readable medium encoded with a computer program for causing a processor to perform a method for detecting or monitoring a dental condition of a patient's teeth, wherein the method comprises:

obtaining a first digital 3D representation of the teeth recorded at a first point in time and segmenting the first digital 3D representation such that a first 3D tooth model is formed for at least one tooth;

obtaining a second digital 3D representation of the teeth recorded at a second point in time and segmenting the second digital 3D representation such that a second 3D tooth model is formed for the least one tooth;

aligning the first and second 3D tooth models;

comparing one or more corresponding regions on the aligned first and second 3D tooth models; and subsequently detecting a change in a parameter representing a dental condition based on the comparison, wherein, when a detected change exceeds a set threshold, an operator is prompted through a graphical user interface;

wherein the user interface is configured to visualize the change in the parameter by aligning the digital 3D representations and then controlling a transparency of the different digital 3D representations based on an order in which the digital 3D representations are obtained;

wherein the dental condition is caries, and wherein the detecting comprises:

detecting a change in color in the digital 3D tooth models between the one or more corresponding regions on the aligned first and second digital 3D tooth models, wherein a detected change in color is correlated with an expected change in the color in response to the development of caries.

2. The non-transitory computer readable medium of claim 1, wherein the operator is prompted with a notification on the graphical user interface.

3. The non-transitory computer readable medium of claim 1, wherein when the detected change reaches a set threshold value defined by a darkening color change, the detected change triggers prompting the operator.

4. The non-transitory computer readable medium of claim 1, wherein the detecting comprises determining a color difference map for the one or more corresponding regions by comparing the color data of the one or more corresponding regions.

5. The non-transitory computer readable medium of claim 1, wherein the detecting comprises selecting a region of interest as the one or more corresponding regions, wherein the detecting comprises determining a color value for at least said region of interest in the first and second digital 3D tooth models and determining the change in the color value between the first and second digital 3D tooth models.

6. The non-transitory computer readable medium of claim 1, wherein the alignment is based on at least two teeth in the digital 3D representation, such as the neighboring teeth.

7. The non-transitory computer readable medium of claim 1, wherein aligning is based on the patient's rugae.

8. The non-transitory computer readable medium of claim 1, wherein aligning the first and second 3D tooth models comprises determining a transformation matrix which provides the alignment, and where distances are derived from the transformation matrix.

9. A system comprising a non-transitory computer readable medium encoded with a computer program for causing a processor to perform a method for visualize a change in a dental condition of a patient's set of teeth and a graphical user interface, wherein the graphical user interface is configured to visualize the change in a dental condition of a patient's set of teeth by the method, the method comprising:

obtaining a first digital 3D representation of the teeth recorded at a first point in time;

obtaining a second digital 3D representation of the teeth recorded at a second point in time;

comparing at least parts of the first and second digital 3D representations; and detecting, based on the comparison, a change in a parameter relating to the dental condition, wherein, when a change exceeding a set threshold is detected, an operator is prompted through the graphical user interface;

wherein the graphical user interface is configured to visualize a development of a dental condition by aligning the digital 3D representations and then controlling transparency of the digital 3D representations based on an order in which the digital 3D representations are obtained wherein the dental condition is caries, and wherein the detecting comprises:

detecting a change in color in the digital 3D tooth models between the one or more corresponding regions on the aligned first and second digital 3D tooth models, wherein a detected change in color is correlated with an expected change in the color in response to the development of caries.

10. The system of claim 9, wherein the graphical user interface is configured to visualize a change in color over different parts of the patient's teeth by displaying a difference map.

11. A method for detecting or monitoring a dental condition of a patient's teeth, the method comprising:

obtaining a first digital 3D representation of the teeth recorded at a first point in time and segmenting the first digital 3D representation such that a first 3D tooth model is formed for at least one tooth;

obtaining a second digital 3D representation of the teeth recorded at a second point in time and segmenting the second digital 3D representation such that a second 3D tooth model is formed for the least one tooth;

aligning the first and second 3D tooth models;

comparing one or more corresponding regions on the aligned first and second 3D tooth models;

subsequently detecting a change in a parameter representing a dental condition based on the comparison; and prompting an operator through a graphical user interface when a detected change exceeds a set threshold;

wherein the user interface is configured to visualize the change in the parameter by aligning the digital 3D representations and then controlling a transparency of the different digital 3D representations based on an order in which the digital 3D representations are obtained;

wherein the dental condition is caries, and wherein the detecting comprises:

detecting a change in color in the digital 3D tooth models between the one or more corresponding regions on the aligned first and second digital 3D tooth models, wherein a detected change in color is correlated with an expected change in the color in response to the development of caries.

12. The method of claim 11, wherein the operator is prompted with a notification on the graphical user interface.

13. The method of claim 11, wherein when the detected change reaches a set threshold value defined by a darkening color change, the detected change triggers prompting the operator.

14. The method of claim 11, wherein the detecting comprises determining a color difference map for the one or more corresponding regions by comparing the color data of the one or more corresponding regions.

15. The method of claim 11, wherein the detecting comprises selecting a region of interest as the one or more corresponding regions, wherein the detecting comprises determining a color value for at least said region of interest in the first and second digital 3D tooth models and determining the change in the color value between the first and second digital 3D tooth models.

16. The method of claim 11, wherein the alignment is based on at least two teeth in the digital 3D representation, such as the neighboring teeth.

17. The method of claim 11, wherein aligning is based on the patient's rugae.

18. The method of claim 11, wherein aligning the first and second 3D tooth models comprises determining a transformation matrix which provides the alignment, and where distances are derived from the transformation matrix.

19. A system comprising:

a non-transitory computer readable medium encoded with a computer program for causing a processor to perform a method for visualize a change in a dental condition of a patient's set of teeth; and a graphical user interface, wherein the method comprises:

obtaining a first digital 3D representation of the teeth recorded at a first point in time and segmenting the first digital 3D representation such that a first 3D tooth model is formed for at least one tooth;

obtaining a second digital 3D representation of the teeth recorded at a second point in time and segmenting the second digital 3D representation such that a second 3D tooth model is formed for the least one tooth;

aligning the first and second 3D tooth models;

comparing one or more corresponding regions on the aligned first and second 3D tooth models; and subsequently detecting a change in a parameter representing a dental condition based on the comparison, wherein, when a detected change exceeds a set threshold, an operator is prompted through the graphical user interface;

wherein the user interface is configured to visualize the change in the parameter by aligning the digital 3D representations and then controlling a transparency of the different digital 3D representations based on an order in which the digital 3D representations are obtained;

wherein the dental condition is caries, and wherein the detecting comprises:

detecting a change in color in the digital 3D tooth models between the one or more corresponding regions on the aligned first and second digital 3D tooth models, wherein a detected change in color is correlated with an expected change in the color in response to the development of caries.

20. The system of claim 19, wherein the operator is prompted with a notification on the graphical user interface.

21. The system of claim 19, wherein when the detected change reaches a set threshold value defined by a darkening color change, the detected change triggers prompting the operator.

22. The system of claim 19, wherein the detecting comprises determining a color or shade difference map for the one or more corresponding regions by comparing the shade data or color data of the one or more corresponding regions.

23. The system of claim 19, wherein the detecting comprises selecting a region of interest as the one or more corresponding regions, wherein the detecting comprises determining a color value for at least said region of interest in the first and second digital 3D tooth models and determining the change in the color value between the first and second digital 3D tooth models.

24. The system of claim 19, wherein the alignment is based on at least two teeth in the digital 3D representation, such as the neighboring teeth.

25. The system of claim 19, wherein aligning is based on the patient's rugae.

26. The system of claim 19, wherein aligning the first and second 3D tooth models comprises determining a transformation matrix which provides the alignment, and where distances are derived from the transformation matrix.

* * * * *